Figure 1:
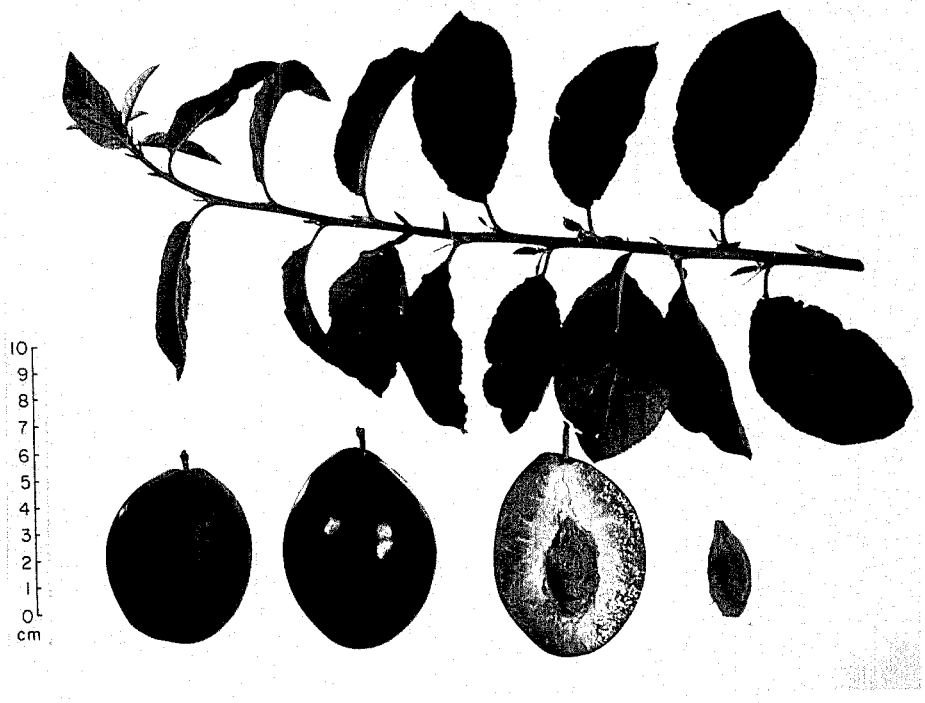

US00PP08188P

United States Patent [19]

Doyle et al.

[11] Patent Number: Plant 8,188

[45] Date of Patent: Mar. 30, 1993

[54] PLUM TREE CALLED 'EMPEROR'

[75] Inventors: James F. Doyle, Clovis; Theodore M. De Jong, Davis, both of Calif.

[73] Assignee: The Regents of the University of California, Berkeley, Calif.

[21] Appl. No.: 758,037

[22] Filed: Sep. 12, 1991

[51] Int. Cl.[5] ..... A01H 5/00

[52] U.S. Cl. ..... Plt./38.1

[58] Field of Search ..... Plt./38, 38.1

[56] References Cited

U.S. PATENT DOCUMENTS

P.P. 3,862 4/1976 Odier ..... Plt. 38.2
P.P. 4,053 5/1977 Adrich ..... Plt. 38.2
P.P. 4,232 4/1978 Friedman et al. ..... Plt. 38.2

*Primary Examiner*—James R. Feyrer
*Attorney, Agent, or Firm*—Townsend and Townsend

[57] ABSTRACT

The 'Emperor' is a large, blue, midseason plum with high quality and high productivity. To date, the selection has been tolerant of high summer temperatures in both the tree and the fruit. The plum has substantial potential for widespread domestic use, as well as for the export market.

1 Drawing Sheet

DESCRIPTION

This invention relates to a new and useful variety of plum tree (*Prunus domestica,* European Plum) named 'Emperor'. The plum selection, originally designated KAC 5-6-38 has resulted from an open-pollinated seed of U.C. selection 11,15-27. The 11,15-27 was an isolated European plum tree located in Block 54B at the Kearney Agricultural Center, Parlier, Calif. In March of 1985, a large bouquet of flowers consisting of five prune selections (D2-3-35, D2-8-4, D-3-11, D3-93 and D10-70), all seedlings of the Improved French Prune, was hung in the parent tree of 11,15-27. The intention of the inventors was to effect cross pollination between the parent 11,15-27 and the five seedlings of Improved French Prune. The parentage of 11,15-27 is an open pollinated seedling of UC selection 15-16 (PA3-82; a cross of 'Burton' by Yakima).

Seed was collected from the fruit produced on the 11,15-27 tree in 1985, and a population of 36 seedlings was grown from this seed in spring of 1986. The seedling population was assigned the population number 86.2 and was planted along with 1,616 other plum seedlings in seedling block 502-5 at the Kearney Agricultural Center.

In spring of 1987 a partial tree of 5-6-38 was propagated on 'Marianna 2624' rootstock. The seedling 5-6-38 had grown extremely well in the seedling block, far more vigorously than any other seedling in the block. It was thought by the inventors that 5-6-38 might have some potential as a rootstock and so, even before fruit was borne on the original seedling, a partial tree of 5-6-38 was propagated to increase the amount of wood available to make cuttings. Subsequently it was discovered that cuttings of 5-6-38 were difficult to root, so its rootstock potential was not pursued further.

The original seedling of 5-6-38 first fruited in 1988 in Block 502-5 at Kearney. Due to the vigor of the tree, the very large fruit size and the superior quality of the fruit produced on 5-6-38, the selection was made and designated for further testing in August of 1988. (A small grower-cooperator test plot was established in 1989) and additional propagation took place in the prune selection block at Kearney in 1989. This propagation was accomplished by grafting onto existing four year old 'Marianna' plum rootstock.

IN THE DRAWINGS

FIG. 1 shows leaves, pit, flesh and whole fruit typical of the new variety. Also shown are the typical fruit apex and suture line of the new variety depicted by the plum with the waxy grey bloom adjacent the ruler in the photograph.

Currently virus tested trees of 'Emperor' are maintained at Foundation Plant Materials Service at UC Davis. The potential for utilization of this European plum selection in the fresh fruit industry is substantial. In California, the predominant cultivars grown for the fresh market are of *Prunus salicina* origin, referred to as "Japanese" types. A few "European" or *Prunus domestica* types are being grown such as 'President', 'Empress', 'Standard' and 'Emily'. Although popular in the marketplace throughout the U.S. and Europe, European plum production has been limited in California because of heat damage to the fruit and tree, as well as poor fruit quality in existing adapted cultivars. Prune cultivars are currently being grown in California as fresh market plums, especially for export to Pacific Rim countries. These cultivars such as 'French', 'Moyer' and 'Sugar', although also of *Prunus domestica* origin, are much more tolerant of high summer temperatures in both fruit and tree. These prune cultivars, although of high quality, are small in size and in heavy crop years few attain the size necessary for packing.

'Emperor' appears to have overcome many of these problems. So far, the new variety demonstrates good tolerance to heat in both the fruit and tree, and produces abundant crops of large size fruit. Fruit quality to date has been superior to most European plum cultivars grown for fresh market in California.

The European plum is more widely adapted to a range of growing conditions than the Japanese plum. European plums have been grown commercially in the Eastern U.S. and in areas of Europe where the Japanese plum, because of a range of disease and climatic problems, has met with little or no success. 'Emperor' appears to have the potential for use in the traditional "Japanese" plum growing areas of California as well as use in areas of the U.S. and Europe where the European plum is adapted.

While the putative parent of 'Emperor' is a prune, 'Emperor' is not. 'Emperor' does not accumulate sugar readings of 22° Brix or over and does not try naturally without fermentation. Accordingly the fruit of 'Emperor' is considered a fresh market plum.

SPECIFIC DESCRIPTION

The following description was developed from fruit and plant material obtained from several propagated trees of 'Emperor'; the fruit produced on these young trees represent the upper size limits of the cultivar; the fruit was described at a full, firm ripe maturity in early August of 1990; color definitions are from "Dictionary of Color" by Maerz and Paul, published in 1950:

Tree: Large in size with upright to upright-spreading growth habit. Eventual tree form the density determined by pruning. Tree very vigorous, very productive and hardy under normal Central San Joaquin Valley Climatic conditions. The tree is a regular bearer.

Trunk and branches: Trunk is medium in thickness with medium surface texture and a moderate amount of scarfskin. Branches are long and vigorous. Young limbs and shoots are somewhat netted in surface texture with a russeted epidermis. Color of bark of two year old shoots a bay brown (7-E-11). Color of surface of one year old shoots is light fern green (21-F-5), with exposed shoots turning a reddish brown (6-I-8) especially late in the growing season. Bark lenticels are small and relatively few on one and two year old wood. Lenticels are large in size and relatively numerous on the tree trunk. One year shoots are moderately pubescent.

Leaves: Medium to large in size. Leaf dimension measurements were taken from large vigorous leaves growing at midpoint of upright shoots in the crown of the tree. Leaf length averages 11.3 cm. including the petiole. Leaf width averages 6.3 cm.

*Leaf form.*—Oval to at times slightly obovate in form. Leaf apex acute. Leaves are relatively flat to at times slightly rolled downwards along the margins.

*Leaf color.*—Upper leaf surface a dark green (23-E-9). Lower leaf surface a light grey-green (21-G-6). Leaf vein on underside of leaf a pale green (19-H-3). The overall upper leaf surface is moderatley glossy.

*Leaf margins.*—Coarsely and somewhat irregularly crenate in form, at times with double crenations, especially near midpoint of the margin.

*Leaf petiole.*—Medium length average ranges from 13 to 18 mm. Medium petiole thickness averaging 2.0 mm. Petiole color a pale green (19-H-3). Petiole surface pubescent. The petiole is usually curved downwards causing the leaves to hang in a drooping position.

*Leaf glands.*—Somewhat variable, but most often one to two small glands present, globose in form and usually borne on a moderately long stalk. Gland position is usually alternate and the gland is located on the petiole just below the base of the leaf margin. Color of glands on young growth is a light shiny green (19-J-6). Glands darken and deteriorate with age.

Stipules: Moderately large in size and lanceolate in form. Average range 8.0 to 12.0 mm in length. Average range 1.5 to 2.5 mm in breadth. Stipule margins are sparsely serrate with large long irregular serration. Stipule color is a light green (21-G-8). Stipules are for the most part persistent late into the season (September and October).

Fruit Description

Maturity: Date of first pick Aug. 2, 1990. Date of last pick Aug. 12, 1990. First pick occurred with fruit at about 7 pounds flesh pressure.

Fruit:

*Size.*—Uniform, very large. Average cheek diameter 55.3 mm, average suture diameter 55.1 mm, average axial diameter 71.3 mm.

*Form.*—Uniform. Lateral aspect oblong to oval. Axial aspect irregular, but most often nearly globose.

*Suture.*—A narrow, shallow, but distinct line from base to apex, dark admiral blue-purple in color (48-E-12) slightly darker than the color of the surrounding skin area. The suture is smooth with almost no stiching present.

*Ventral surface.*—Rounded and relatively smooth. In general, slight to almost no lipping is present, although lipped fruit can occasionally be found. Fruit sides are usually almost equal.

*Stem cavity.*—Very small in size, from 7 to 9 mm in width and 8 to 10 mm in length. Cavity form is globose to very slightly oval. The cavity is shallow, from 2 to 4 mm in depth. Ventral suture narrows and forms a thin folded line within the cavity and over the ventral shoulder of the cavity.

*Base.*—Rounded to very slightly truncate. Fruit base is oblique to fruit axis, shorter on the ventral suture side.

*Apex.*—Generally rounded to slightly domed. Pistil point is apical.

Stem: Medium in length from 9 to 11 mm. Stem is of medium thickness, 2 to 2.5 mm. Stem color a light olive green (fern green 21-F-5). The stem is highly pubescent with short, fine and rigid pubescence. Distal end of the stem often has a slightly fleshy collar where the stem is attached to the fruit. Collar ranges from 3.0 to 4.5 mm in diameter.

Skin: Skin is glabrous. Medium in thickness with a very mild flavor. Skin is tenacious to the flesh at commercial maturity. No observed tendency to crack.

*Color.*—Overall coloration is a dark blue (egg plant 48-H-12) with little variation from base to apex. Lighter areas of a purple-blue color (56-1-2) are present at times, usually over the apical shoulder area. Numerous light colored dots are present over much of the fruit surface. The entire fruit is covered with a waxy grey bloom which, when not removed, gives the fruit an overall light blue appearance.

Flesh:

*Color.*—A uniform amber (Samovar 12-K-7) when fully mature. Less mature fruit have a range of greenish tones present (12-K-4).

*Texture.*—Firm at commercial maturity, becoming soft and juicy with after-ripening.

*Fibers.*—Numerous relatively long, light colored fibers throughout the fruit. Fibers are fine textured and soft.

Ripening: Ripens evenly.

Aroma: Very slight.

Flavor: Mild flavor, sweet, very pleasant. Eating quality is well above average.

Stone:

*Attachment.*—Cling to semi-cling. Tightly held in fruit cavity. Almost no air space apparent.

*Size.*—Medium. Average length 37 to 40 mm, average width 19 to 21 mm, average thickness 12 to 15 mm.

*Fibers.*—Numerous short fibers attached to the stone especially laterally and along ventral suture.

*Form.*—Generally oval with relatively narrow, truncate base.

*Base.*—Narrow, moderately truncate. Base angle can be variable but most often is oblique to the stone axis, shorter on the ventral suture side.

*Hilum.*—Small, narrow and relatively indistinct.

*Apex.*—Smoothly rounded with no tip.

*Sides.*—Variable from equal to slightly unequal.

*Surface.*—Relatively smooth with very low netted ridges, especially laterally. Often one more prominent ridge is present near the apical shoulder and extending from the ventral suture to the apical shoulder laterally.

*Ventral edge.*—Broad, measuring 7 to 8 mm wide at mid-suture. Almost no wings present.

*Dorsal edge.*—A small shallow groove is present upon a rather raised and narrow ridge. Groove is more noticeable basally near mid-suture becoming tighter and less distinct over the apical shoulder.

*Color.*—Dry color a light buff-brown (11-G-7).

*Tendency to split.*—None observed.

Use: A large fresh market European type plum for local market and for long distance shipping.

Inflorescence

The following description of inflorescence was developed from flowers borne on several propagated trees of 'Emperor' growing in Block 502N at the Kearney Agricultural Center, Parlier, Calif. The description was made in March, 1991. Numbers of chilling hours compiled at this location was 1140 hours at or below 45° F. for the 1990 to 1991 winter season. This represents an average chilling season for this location.

Bloom:

*Timing.*—Average to slightly early in relation to other cultivars of *Prunus domestica.* The date of full bloom for 'Emperor' was Mar. 23, 1991. Dates of full bloom for other plum cultivars at Kearney in 1991 are: Stanley — March 19; Improved French Prune — March 26; Santa Rosa (*Prunus salicina*) — Feb. 25, 1991.

*Flower Size.*—Medium to large for the species. Average flower diameter is 19 mm when fully expanded.

*Quantity.*—Abundant, from two to as many as four flowers per node. Bloom development is precocious, especially for *P. domestica,* with many flowers produced on one year old wood.

Flower buds and scales: Color of bud scales is brown (Montella Brown 8-J-11). Buds of medium size and conic in form. Bud surface is pubescent with a short grey publescence.

Petals:

Five in number and of medium size. Average petal length 9.5 mm, average petal width 8.0 mm. The petal form is somewhat variable, from oval to slightly ovate. Petal color is white. The petal claw is very short and truncate. Petal margins are only slightly undulate. Petal apices are generally rounded with no tip.

Pedicel: Medium in length, averaging 7.0 mm. Pedicel thickness is average, 1.0 mm. Pedicel color is a medium green (10-L-7). Pedicel surface is densely covered with a short erect pubescence.

Nectaries: Color a greenish-brown (old moss 14-L-2). Nectar abundant.

Anthers: Medium in size, very plump, with a bright yellow color (Aureolin yellow 10-L-2).

Pollen: Abundant. Pollen color a bright yellow (10-L-3).

Stamens: Medium in length. Stamens are slightly shorter than the pistil at full extension. Filaments are white in color.

Pistil: Average length is 9.5 mm including the ovary. Pistil color is it light green-yellow (19-J-2). Ovary color is a darker, shiny green (Calliste green 19-L-6). The ovary is glabrous, but the basal one quarter of the style is covered with rather long, filamentous hairs.

We claim:

1. The new and distinct variety of plum tree herein described and illustrated and identified by the characteristics above enumerated.

* * * * *